United States Patent [19]

Pfister et al.

[11] Patent Number: 4,670,040
[45] Date of Patent: Jun. 2, 1987

[54] PHENOXYPROPIONYLOXYALKANE PHOSPHONATES

[75] Inventors: Theodor Pfister, Monheim; Heinz Förster, Wuppertal; Ludwig Eue, Leverkusen; Robert R. Schmidt, Bergisch-Gladbach; Hans-Joachim Santel, Cologne, all of Fed. Rep. of Germany

[73] Assignee: Bayer Aktiengesellschaft, Leverkusen, Fed. Rep. of Germany

[21] Appl. No.: 694,548

[22] Filed: Jan. 24, 1985

[30] Foreign Application Priority Data

Jan. 28, 1984 [DE] Fed. Rep. of Germany ....... 3402982

[51] Int. Cl.4 .................. C07F 9/58; A01N 43/40
[52] U.S. Cl. ............................. 71/86; 71/94; 546/24; 546/22
[58] Field of Search ............ 546/24; 71/94, 86

[56] References Cited

U.S. PATENT DOCUMENTS 4,326,880  4/1982  Rempfler ............................ 71/94
4,425,156  1/1984  Pissiotas et al. ................... 71/94
4,470,841  9/1984  Sasaki et al. ....................... 71/86

FOREIGN PATENT DOCUMENTS 0073040   3/1983  European Pat. Off. ............ 71/86
0096354  12/1983  European Pat. Off. ............ 546/14
0121871  10/1984  European Pat. Off. ............ 546/22

Primary Examiner—Alan L. Rotman
Attorney, Agent, or Firm—Sprung Horn Kramer & Woods

[57] ABSTRACT

Novel phenoxypropionyloxyalkanephosphonates of the formula

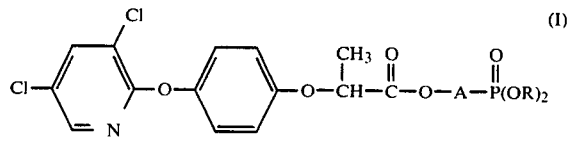

in which
R is optionally substituted alkyl and
A is optionally substituted alkanediyl,
and the use of such new compounds as herbicides.

10 Claims, No Drawings

PHENOXYPROPIONYLOXYALKANE PHOSPHONATES

The present invention relates to new phenoxyproplonyloxyalkanephosphonates, to herbicidal compositions containing them, and to their use as herbicides.

It has been disclosed that a large number of phenoxypropionic acid derivatives possess herbicidal properties (see DE-OS (German Published Specification) No. 2,223,894). Thus, for example, methyl 2-[4-(2,4-dichlorophenoxy)-phenoxy]-propionate can be employed for combating weeds. However, the action of this substance is not always adequate, particularly when low application rates are employed.

The present invention now provides as new compounds, the phenoxypropionyloxyalkanephosphonates of the formula

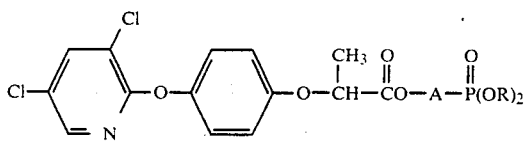

in which
R represents optionally substituted alkyl and
A represents optionally substituted alkanediyl.

The phenoxypropionyloxyalkanephosphonates of the formula (I) contain at least one asymmetrically substituted carbon atom and can therefore occur in different enantiomeric forms. The invention relates both to the possible individual isomers and to mixtures of these isomers.

The present invention also provides a process for the preparation of a phenoxypropionyloxyalkanephosphonate of the formula (I), whioh process comprises (a) reacting a 2[4-(3,5-diohloropyridin-2-yl-oxy)-phenoxy] -propionyl chloride of the formula

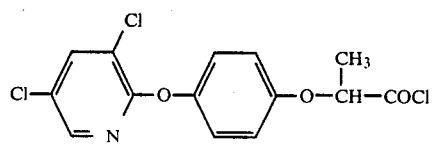

with a hydroxyalkanephosphonate of the formula

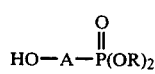

in which R and A have the above mentioned meanings, if appropriate in the presence of an acid acceptor and, if appropriate, in the presence of a diluent, or (b) reacting a hydroxyalkanephosphonate of the formula

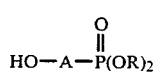

in which R and A have the meanings given above, with a halogenopropionyl halide of the formula

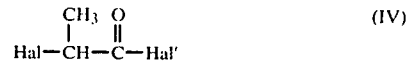

in which Hal and Hal' independently of one another represent chlorine or bromine, if appropriate in the presence of an acid-binding agent and, if appropriate, in the presence of a diluent, and reacting the resulting propionyloxyalkanephosphonate of the formula

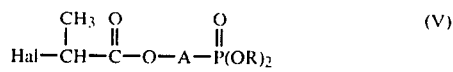

in which R, A and Hal have the meanings given above, are reacted with 4-(3,5-dichloro-pyridine-2-yloxy)-phenol of the formula (VI)

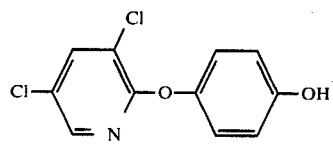

if appropriate in the presence of an acid-binding agent and, if appropriate, in the presence of a diluent.

Finally, it has been found that the phenoxypropionyloxyalkanephosphonates of the formula (I) are distinguished by outstanding herbicidal activity.

Surprisingly, the phenoxypropionyloxyalkanephosphonates according to the invention, of the formula (I), possess substantially better herbicidal properties than methyl 2-[4-(2,4-dichlorophenoxy)-phenoxy]-propionate, which is known from the prior art and which is a highly effective active compound having the same type of action.

Formula (I) gives an unambiguous definition of the phenoxypropionyloxyalkanephosphonates according to the invention. In this formula, R preferably represents alkyl which is optionally substituted by halogen and has 1 to 6 carbon atoms, and A preferably represents optionally substituted alkanediyl having 1 to 6 carbon atoms. Substituents which are preferred are: alkyl having 1 to 4 carbon atoms or pyridyl, or phenyl which is optionally monosubstituted to trisubstituted by fluorine, chlorine, bromine, nitro, $C_1$–$C_4$-alkyl, $C_1$–$C_4$-alkoxy, halogeno-$C_1$–$C_4$-alkyl, halogeno-$C_1$–$C_4$-alkoxy, phenoxy, and/or methylenedioxy.

Particularly preferred compounds of the formula (I) are those in which

R represents ethyl, n-propyl, i-propyl, n-butyl, i-butyl, sec.-butyl, tert.-butyl or methyl which is optionally substituted by chlorine or bromine, and A represents $C_1$–$C_2$-alkanediyl which can optionally be substituted by $C_1$–$C_4$-alkyl, pyridyl or by phenyl which is optionally monosubstituted to trisubstituted by fluorine, chlorine, bromine, nitro, $C_1$–$C_4$-alkyl, $C_1$–$C_2$-alkoxy, trifluoromethyl, trifluoromethoxy, phenoxy and/or methylenedioxy.

As already mentioned above, the compounds according to the invention contain at least one asymmetrically substituted carbon atom in the side chain, and can therefore occur in two enantiomeric forms. In the formula below, the asymmetrically substituted carbon atom is designated by an (*).

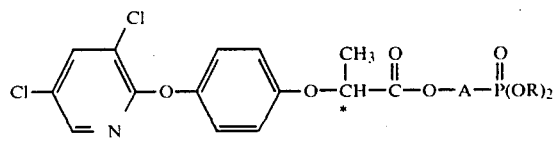

The invention relates both to the particular racemates and to the R and S enantiomers.

In the present context, R enantiomers (S enantiomers) are understood in each case as meaning those optically active compounds which have the R configuration (S configuration) at the asymmetrically substituted carbon atom of the propionic acid unit.

Particularly preferred R enantiomers are those of the phenoxypropionyloxyalkanephosphonates of the formula (I) in which R and A have the meanings which are stated above as being particularly preferred.

If 2-[4-(3,5-dichloro-pyridin-2-yloxy)-phenoxy]-propionyl chloride and dimethyl 2-hydroxyethanephosphonate are used as starting materials, the course of process (a) according to the invention can be represented by the following equation:

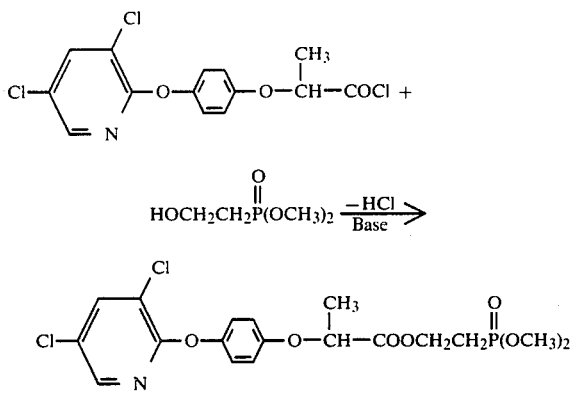

If diethyl 2-hydroxyethane-phosphonate and 2-chloro-propionyl chloride are used as starting materials, and 4-(3,5-dichloro-pyridin-2-yloxy)-phenol is used as a reactant, the course of process (b) according to the invention can be represented by the following equation:

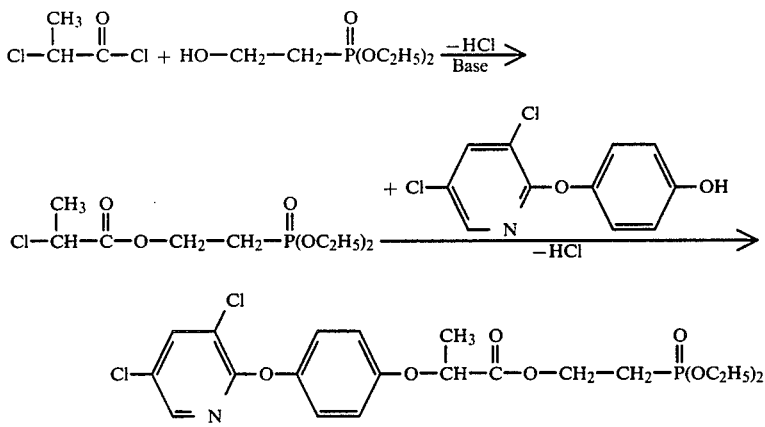

The 2-[4-(3,5-dichloro-pyridin-2-yloxy)-phenoxy]-propionyl chloride of the formula (II) which is required as a starting material for carrying out process (a) according to the invention is known (see DE-OS (German Published Specification) No. 2,546,251).

To prepare R and S enantiomers of the phenoxypropionyl-oxyalkane-phosphonates of the formula (I), the R and the S enantiomers respectively, of 2-[4-(3,5-dichloropyridin-2-yloxy)-phenoxy]-propionyl chloride of the formula (II) are required for carrying out process (a) according to the invention.

The R and S enantiomers of 2-[4-(3,5-dichloropyridin-2-yloxy)-phenoxy]-propionyl chloride of the formula

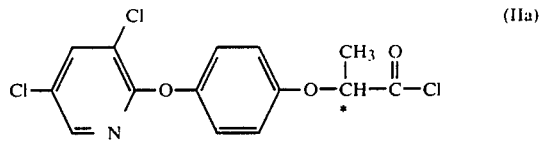

(IIa)

are obtained by reacting 4-(3,5-dichloro-pyridin-2-yloxy)-phenol of the formula

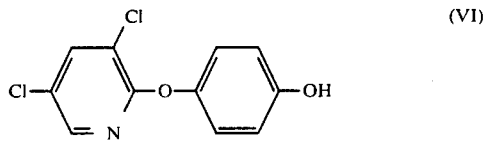

(VI)

with, respectively, the S enantiomers and R enantiomers of propionic acid derivatives of the formula

(VII)

in which

R¹ represents methyl or ethyl, and

Q represents chlorine, bromine, mesylate or tosylate, if appropriate in the presence of an acid acceptor, such as, for example, potassium carbonate, and, if appropriate, in the presence of a diluent, such as, for example, acetonitrile, at temperatures between 0° C. and 120° C., hydrolysing the resulting esters of the formula

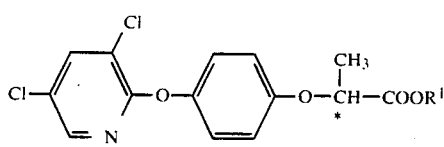

in which R¹ has the meaning given above,
with strong bases, such as, for example, sodium hydroxide, in the presence of a diluent, such as, for example, methanol, ethanol, benzene, toluene or xylene, if appropriate as a mixture with water, at temperatures between 20° C. and 140° C., then acidifying the product with an acid, such as, for example, hydrochloric acid, and reacting the resulting enantiomeric acids of the formula

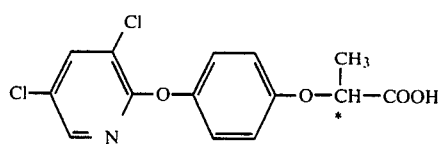

with chlorinating agents, such as, for example, thionyl chloride, if appropriate in the presence of an inert diluent, such as, for example, tetrachloromethane, and, if appropriate, in the presence of a catalyst, such as, for example, dimethylformamide, at temperatures between 20° C. and 100° C.

In the first stage of this reaction, a Walden inversion takes place at the asymmetrically substituted carbon atom of the propionic acid unit. Because of this, reaction of 4-(3,5-dichloropyridin-2-yloxy)-phenol of the formula (VI) with the S enantiomers of the propionic acid derivatives of the formula (VII) results in the formation of the R enantiomer of 2-[4-(3,5-dichloropyridin-2-yloxy)-phenoxy]-propionyl chloride of the formula (II). On the other hand, reaction of 4-(3,5-dichloropyridin-2-yloxy)-phenol of the formula (VI) with the R enantiomers of the propionic acid derivatives of the formula (VII) results in the formation of the S enantiomer of 2-[4-(3,5-dichloro-pyridin-2-yloxy)-phenoxy]-propionyl chloride of the formula (II).

Formula (III) gives a definition of the hydroxyalkanephosphonates furthermore required as starting materials in process (a) according to the invention. In this formula, R and A preferably have those meanings which have been mentioned in connection with the description of the substances according to the invention, of the formula (I), as being preferred.

The following may be mentioned individually as examples of the compounds of the formula (III):

TABLE 1

$$HO-A-\overset{\overset{O}{\|}}{P}(OR)_2 \qquad (III)$$

| A | R | A | R | A | R |
|---|---|---|---|---|---|
| —CH₂— | CH₃ | —CH— | CH₃ | —CH— | CH₃ |
| —CH— | CH₃ | \|  | | \| | |
| \| | | CH₃ | | (pyridyl) | C₂H₅ |
| C₂H₅ | | —CH— | C₂H₅ | | |
| | | \| | | | |
| | | CH₃ | | | |
| —CH— | CH₃ | —CH₂CH₂— | CH₃ | —CH— | CH₃ |
| \| | | | | \| | |
| C₃H₇—i | | | | (phenyl) | C₂H₅ |
| —CH— | CH₃ | —CH₂CH₂— | C₂H₅ | | |
| \| | | | | | |
| C₃H₇—n | | | | —Cl | |
| —CH— | CH₃ | —CH— | C₂H₅ | —CH— | CH₃ |
| \| | | \| | | \| | |
| (phenyl) | | C₂H₅ | | (2,4-diClphenyl) | |
| | | —CH— | C₂H₅ | | |
| | | \| | | | |
| | | C₃H₇—n | | | |
| —CH— | CH₃ | —CH— | C₂H₅ | —CH— | C₂H₅ |
| \| | | \| | | \| | |
| (4-CF₃-phenyl) | | C₃H₇—iso | | (3-phenoxyphenyl) | |
| —CH₂— | C₂H₅ | —CH— | C₂H₅ | | |
| | | \| | | | |
| | | (phenyl) | | | |
| —CH₂— | CH₂CH₂Cl | —CH— | CH₃ | —CH— | C₂H₅ |
| —CH₂— | C₃H₇—n | \| | | \| | |
| | | (2-Cl-phenyl) | | (4-OCH₃-phenyl) | |

TABLE 1-continued $$HO-A-\overset{\overset{O}{\|}}{P}(OR)_2 \quad (III)$$

| A | R | A | R | A | R |
|---|---|---|---|---|---|
| —CH₂— | C₃H₇—iso | —CH—  | CH₃ | —CH—  | CH₃ |
| —CH₂— | C₄H₉—n | | | | |
| —CH₂— | C₄H₉—iso | | | | |

The hydroxyalkanephosphonates of the formula (III) are known (see Synthesis 1982, 165–166, 653–655 and 916, and DE-OS (German Published Specification) No.3,021,264).

Process (a) for the preparation of the new compounds of the formula (I) is preferably carried out using suitable diluents. Suitable diluents are virtually all inert organic solvents. These include, in particular, aliphatic and aromatic, optionally halogenated hydrocarbons, such as pentane, hexane, heptane, cyclohexane, benzene, toluene, xylene, methylene chloride, chloroform, carbon tetrachloride, chlorobenzene and dichlorobenzene, ethers, such as diethyl ether, diisopropyl ether, 1,2-dimethoxy-ethane, tetrahydrofuran and dioxane, esters, such as methyl acetate and ethyl acetate, nitriles, such as acetonitrile and propionitrile, amides, such as dimethylformamide and dimethylacetamide, and dimethyl sulphoxide and sulpholane.

Process (a) according to the invention is preferably carried out in the presence of acid acceptors. Suitable acid acceptors are virtually all customary acid-binding agents. Alkali metal and alkaline earth metal hydroxides, such as, for example, sodium hydroxide, potassium hydroxide and calcium hydroxide, alkali metal and alkaline earth metal carbonates and bicarbonates, such as, for example, sodium carbonate and bicarbonate, potassium carbonate and calcium carbonate, and aliphatic, aromatic and heterocyclic amines, such as, for example, trimethyl-, triethyl-, tripropyl- and tributyl-amine, N,N-dimethylbenzylamine, pyridine, 2-methyl-pyridine, 2,4,6-trimethylpyridine, 2-methyl-5-ethyl-pyridine, diazabicyclooctane (DABCO), diazabicyclononene (DBN) and diazabicycloundecene (DBU), can be particularly preferably used.

In process (a), the reaction temperatures can be varied within a relatively wide range. In general, the reaction is carried out at temperatures between −50° C. and +100° C., preferably between −20° C. and +50° C.

Process (a) is carried out in general under atmospheric pressure.

To carry out process (a) according to the invention, in general between 0.8 and 1.5 mol, preferably between 1.0 and 1.3 mol, of the starting compound of the formula (III) are employed per mol of starting compound of the formula (II).

The components are usually combined while cooling slightly, and the reaction mixture is stirred until the reaction is complete.

Working-up can be carried out by customary methods, for example by shaking the reaction mixture with aqueous sodium bicarbonate solution and a virtually water-immiscible organic solvent, such as, for example, methylene chloride, drying and filtering the organic phase, and carefully distilling off volatile components under reduced pressure, the products of the formula (I) remaining in the residue.

The hydroxyalkanephosphonates required as starting materials in process (b) according to the invention have already been discussed in connection with the description of process (a) according to the invention.

Formula (IV) gives an unambiguous definition of the halogenopropionyl halides furthermore required as starting materials in process (b) according to the invention. In this formula, Hal and Hal' independently of one another represent chlorine or bromine.

The halogenopropionyl halides of the formula (IV) are known.

To prepare optically active compounds of the formula (I), the R or S enantiomers of the halogenopropionyl halides of the formula (IV) are required for carrying out process (b) according to the invention. These substances are known, or can be prepared in a known manner, by customary methods.

Reaction of the R or S enantiomers of the halogenopropionyl halides of the formula (IV) with hydroxyalkanephosphonates of the formula (III) gives the corresponding optically active propionyloxyalkanephosphonates of the formula (V), which are then brought to reaction, in the second stage of process (b) according to the invention, with 4-(3,5-dichloropyridin-2-yloxy)-phenol of the formula (VI). In this second stage, the Walden inversion once again takes place at the asymmetrically substituted carbon atom.

The 4-(3,5-dichloro-pyridin-2-yloxy)-phenol of the formula (VI) required as a reactant for carrying out process (b) according to the invention is known (see DE-OS (German Published Specification) No. 2,758,002 and DE-OS (German Published Specification) No. 2,546,251).

The following may be mentioned individually as examples of the propionyloxyalkanephosphonates of the formula (V) which are obtained as intermediate products in process (b) according to the invention:

dimethyl, diethyl, di-n-propyl, di-iso-propyl, di-n-butyl and di-iso-butyl 2-chloro- and 2-bromo-propionyloxymethanephosphonate;

dimethyl, diethyl, di-n-propyl, di-iso-propyl, di-n-butyl and di-iso-butyl 1-(2-chloro-propionyloxy)- and 1-(2-bromo-propionyloxy)-ethanephosphonate;

dimethyl and diethyl 1-(2-chloro-propionyloxy)- and 1-(2-bromo-propionyloxy)-propanephosphonate;

dimethyl and diethyl 1-(2-chloro-propionyloxy)- and 1-(2-bromo-propionyloxy)-butanephosphonate and dimethyl and diethyl 2-chloro-propionyloxy- and 2-bromo-propionyloxyphenylmethanephosphonate.

Some of the propionyloxyalkanephosphonates of the formula (V) are known (see EP-OS (European Published Specification) No. 0,073,040).

In carrying out process (b) according to the invention, both the first stage and the second stage are preferably carried out in the presence of an acid-binding agent and in the presence of a diluent. Preferred acid acceptors and diluents for carrying out the first stage of process (b) according to the invention are those acid-binding agents and organic solvents which have already been mentioned in connection with the description of process (a) according to the invention. In this context, triethylamine and methylene chloride may be mentioned as examples of acid-binding agents and solvents.

In carrying out the second stage of process (b) according to the invention, strongly basic but weakly nucleophilic substances can preferably be employed as acid acceptors. Sodium hydride, potassium hydride, calcium hydride, sodium carbonate, potassium carbonate and calcium carbonate and diazabicyclooctane (DABCO), diazabicyclononene (DBN) and diazabicycloundecene (DUB) are preferred.

In carrying out the second stage of process (b) according to the invention, aprotic, polar organic solvents can preferably be employed as diluents. Preferred solvents are ketones, such as, for example, acetone, methyl ethyl ketone, methyl isopropyl ketone and methyl isobutyl ketone, nitriles, and furthermore amides, such as dimethylformamide, dimethylacetamide and N-methylpyrrolidone.

In carrying out process (b) according to the invention, too, the reaction temperatures can be varied within a relatively wide range. In general, the first stage is carried out at temperatures between −50° C. and +100° C., preferably between −20° C. and +50 C. The reaction in the second stage is carried out in general at temperatures between 0° C. and 150° C., preferably between 20° C. and 100° C.

Both the first stage and the second stage of process (b) according to the invention are carried out in general under atmospheric pressure.

In carrying out process (b) according to the invention, in general the hydroxyalkanephosphonates of the formula (III) and the halogenopropionyl halides of the formula (IV) are employed in approximately equimolar amounts in the first state. However, it is also possible to use a relatively large excess of one of the two components employed in each case. The reactions are generally carried out in a suitable diluent in the presence of an acid acceptor, and the reaction mixture is stirred for several hours at the required temperature. Working-up and isolation of the propionyloxyalkanephosphonates of the formula (V) are carried out by customary methods. In carrying out the second stage of process (b) according to the invention, in general between 0.8 and 1.5 mol, preferably between 0.95 and 1.2 mol, of the propionyloxyalkanephosphonate of the formula (V) are employed per mol of 4-(3,5-dichloro-pyridin-2-yloxy)-phenol of the formula (VI). The components are combined in general at room temperature, and are stirred at the particular reaction temperature required, until the reaction is complete. Working-up is carried out by customary methods. In general, the procedure is as follows: the reaction mixture is diluted with water, if appropriate after evaporating it down beforehand, and is then extracted with an organic solvent which is only slightly water-miscible, after which the organic phase is dried, and is evaporated down by carefully distilling off volatile components under reduced pressure.

The active compounds according to the invention can be used as defoliants, desiccants and agents for destroying broad-leaved plants, and especially as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be employed for selectively combating grasses in crops such as, for example, cotton, rape, soyabeans and sugar beet, and in cereals, such as, for example, wheat.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is, liquid solvents and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in the form of their formulations, can also be used, for combating weeds, as mixtures with known herbicides, finished formulations or tank mixing being possible.

Suitable herbicides for the mixtures are known herbicides, such as, for example, 1-amino-6-ethylthio-3-(2,2-dimethylpropyl)-1,2,5-triazine-2,4--(1H,3H)-dione or N-(2-benzothiazolyl)-N,N'-dimethyl-urea for combating weeds in cereals, 4-amino-3-methyl-6-phenyl-1,2,4-triazin-5-(4H)-one for combating weeds in sugar beet, and 4-amino-6-(1,1-dimethyl)-3-methylthio-1,2,4-triazin-5-(4H)-one for combating weeds in soya beans. Surprisingly, some of these mixtures also exhibit a synergistic effect.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders and granules. They are used in the customary manner, for example by watering, spraying, atomising or scattering.

The active compounds according to the invention can be applied either before or, in particular, after emergence of the plants.

They can also be incorporated into the soil before sowing.

The amount of active compound used can vary within a substantial range. It depends essentially on the nature of the desired effect. In general, the amounts used are between 0.05 and 10 kg of active compound per ha, preferably between 0.1 and 5.

The present invention also provides a herbicidal composition containing as active ingredient a compound of the formula (I) according to the present invention in admixture with a solid diluent or carrier or in admixture with a liquid diluent or carrier containing a surface-active agent.

The present invention also provides a method of combating weeds which comprises applying to the weeds, or to a habitat thereof, a compound of the formula (I) according to the present invention alone or in the form of a composition containing as active ingredient a compound of the formula (I) according to the present invention in admixture with a diluent or carrier.

The examples which follow illustrate the preparation and the use of the substances according to the invention.

PREPARATION EXAMPLES

EXAMPLE 1

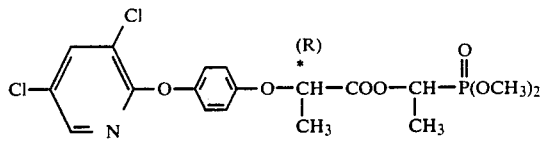

A solution of 11.5 g (0.075 mol) of dimethyl 1-hydroxy-ethanephosphonate in 50 ml of toluene was added dropwise, in the course of one hour, at −15° C., to a stirred solution of 17.3 g (0.05 mol) of the R enantiomer of 2-[4-(3,5-dichloropyridin-2-yloxy)-phenoxy]-propionyl chloride and 7.9 g (0.1 mol) of pyridine in 50 ml of toluene. The reaction mixture was stirred for 4 hours at −15° C. Working-up was then carried out by washing the reaction mixture successively with 5% strength aqueous hydrochloric acid, with aqueous sodium carbonate solution and with water. The organic phase was separated off, dried, and carefully evaporated down under reduced pressure.

18.5 g (80% of theory) of the R enantiomer of dimethyl 2-[4-(3,5-dichloro-pyridin-2-yloxy)-phenoxy]-propionyloxy-ethanephosphonate of refractive index $n_D^{20} = 1.5397$ were obtained.

EXAMPLE 2

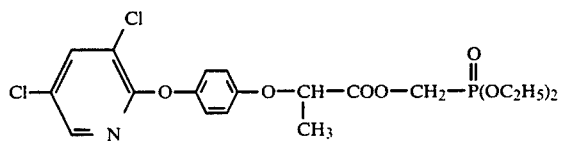

Process variant (a):

A solution of 6.7 g (0.017 mol) of 2-[4-(3,5-dichloropyridin-2-yloxy)-phenoxy]-propionyl chloride in 50 ml of methylene chloride was added dropwise to an ice-cooled mixture of 3.7 g (0.022 mol) of diethyl hydroxy-methanephosphonate, 2.0 g (0.02 mol) of triethylamine and 50 ml of methylene chloride. The reaction mixture was stirred for 15 hours at 20° C. and then washed with aqueous sodium bicarbonate solution The organic phase was separated off, dried, and carefully evaporated down under reduced pressure.

4.1 g (43% of theory) of diethyl 2-[4-(3,5-dichloropyridin-2-yloxy)-phenoxy]-propionyloxy-methanephosphonate of refractive index $n_D^{20} = 1.5327$ were obtained. Preparation of the starting material of the formula:

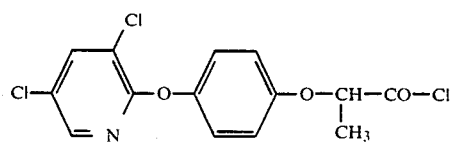

A mixture of 25.6 g (0.07 mol) of 2-[4-(3,5-dichloro-pyrid-2-yloxy)-phenoxy]-propionic acid, 26 g (0.22 mol) of thionyl chloride and one drop of dimethylformamide was heated under reflux for 15 hours. The volatile components were then removed at 60° C. (1 mm Hg).

14.3 g (59% of theory) of 2-[4-(3,5-dichloro-pyrid-2-yloxy)-phenoxy]-propionyl chloride were obtained in this manner.

Preparation process (b):

1st stage:

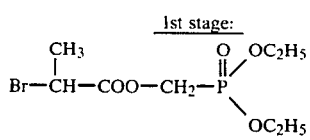

A solution of 8.6 g (0.05 mol) of 2-bromo-propionyl chloride in 30 ml of methylene chloride was added dropwise to a mixture which had been cooled to 0°-10° C. and consisted of 8.4 g (0.05 mol) of diethyl hydroxymethanephosphonate, 6.1 g (0.06 mol) of triethylamine and 30 ml of methylene chloride. The reaction mixture was stirred for 20 hours at 10°-20° C. washed with aqueous sodium bicarbonate solution, dried, filtered, and evaporated down under reduced pressure. 4.9 g (32% of theory) of diethyl 2-bromopropionyloxyme-thanephosphonate were obtained as an oily residue.

2nd stage:

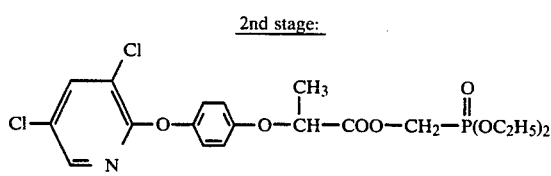

A mixture of 11.5 g (0.045 mol) of 4-(3,5-dichloropyridin-2-yloxy)-phenol, 13.6 g (0.045 mol) of diethyl 2-bromopropionyloxy-methanephosphonate, 15 g of potassium carbonate and 200 ml of acetone was heated to the boil under reflux for 90 minutes and then evaporated down under a vacuum from a water pump, and the residue was diluted with water. The mixture was extracted with toluene, the organic phase was dried and filtered, and the solvent was distilled off under reduced pressure.

9.2 g (43% of theory) of diethyl 2-[4-(3,5-dichloropyridin-2-yloxy)-phenoxy]-propionyloxy-methanephosphonate were obtained as an oily residue.

The compounds listed in Table 2 below were also prepared by the methods given in Examples 1 and 2:

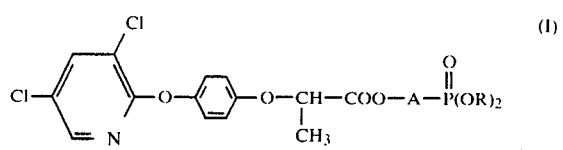

TABLE 2

| Example No. | A | R | Refractive index $n_D^{20}$ |
|---|---|---|---|
| 3 | —CH—<br>\|<br>CH₃ | C₂H₅ | 1.5335 |
| 4 | —CH—<br>\|<br>CH₂CH₃ | C₂H₅ | 1.5372 |
| 5 | —CH—<br>\|<br>CH(CH₃)₂ | C₂H₅ | 1.5257 |
| 6 | —CH—<br>\|<br>CH₂CH₂CH₃ | C₂H₅ | 1.5237 |
| 7 | —CH—(phenyl) | C₂H₅ | 1.5449 |
| 8 | —CH—(2-pyridyl) | CH₃ | 1.5678 |
| 9 | —CH—(4-chlorophenyl) | CH₃ | 1.5594 |
| 10 | —CH—(2,4-dichlorophenyl) | CH₃ | 1.5511 |
| 11 | —CH—(2-chlorophenyl) | C₂H₅ | 1.5455 |

TABLE 2-continued

| Example No. | A | R | Refractive index $n_D^{20}$ |
|---|---|---|---|
| 12 | —CH— (2-pyridyl) | $C_2H_5$ | 1.5459 |
| 13 | —CH— (4-chlorophenyl) | $C_2H_5$ | 1.5521 |
| 14 | —CH— (3-phenoxyphenyl) | $C_2H_5$ | 1.5603 |
| 15 | —CH— (3-nitrophenyl) | $C_2H_5$ | 1.5542 |
| 16 | —CH— (3-nitrophenyl) | $CH_3$ | 1.5564 |
| 17 | —CH— (4-methoxyphenyl) | $CH_3$ | 1.5667 |
| 18 | —CH— (3,4-methylenedioxyphenyl) | $C_2H_5$ | 1.5500 |
| 19 | —CH— (3,4-methylenedioxyphenyl) | $CH(CH_3)_2$ | 1.5432 |

EXAMPLE 20

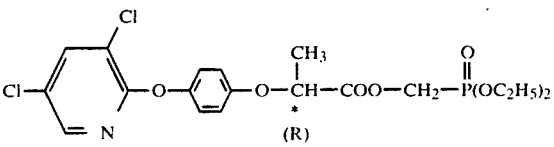

The corresponding diethyl R-2-[4-(3,5-dichloropyridin-2-ylozy)-phenoxy]-propionyloxymethane phosphonate of refractive index $n_D^{20} = 1.5433$ was obtained analogously to Example 2, starting from R-2-[4-(3,5-dichloropyridin-2-yloxy)-phenoxy]-propionyl chloride and diethyl hydroxymethanephosphonate.

EXAMPLE 21

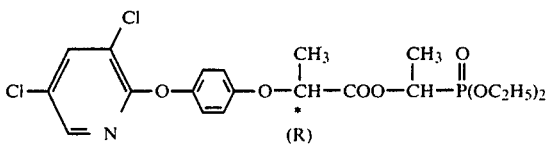

The compound having the structure shown above was also prepared analogously to the procedure given in Example 2.

Yield: 62% of theory.

Refractive index: $n_D^{20} = 1.5351$.

Angle of rotation: $[\alpha]_D^{24} = +12.3°$. (1 molar solution in chloroform; cell length 10 cm).

USE EXAMPLE

In the biological test described below, the following compound was employed as a comparative substance:

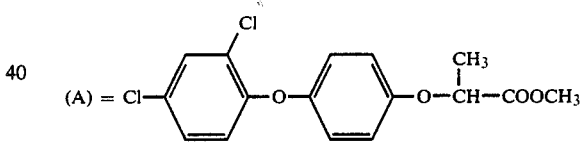

methyl 2-[4-(2,4-dichlorophenoxy)-phenoxy]-propionate (disclosed in DE-OS (German Published Specification) No. 2,223,894).

EXAMPLE A

Post-emergence test

Solvent: 5 parts by weight of acetone.
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control).
100% = total destruction.

In this test, the active compounds according to Example (1) and (2) showed a better selective herbicidal activity than comparative substance (A) in combating Avena fatua, Digitaria, Echinochloa and Setaria in sugar beet, cotton and soya.

It will be understood that the specification and examples are illustrative, but not limitative of the present invention and that other embodiments within the spirit and scope of the invention will suggest themselves to those skilled in the art.

What is claimed is:

1. An R-enantiomer of a phenoxypropionyloxyalkanephosphonate of the formula:

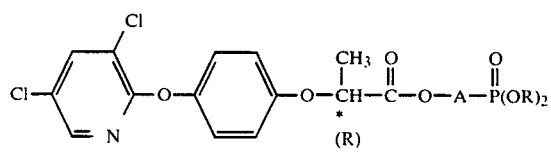

in which R is methyl, ethyl, n-propyl, i-propyl, n-butyl, i-butyl, sec.-butyl, tert-butyl, chloromethyl, chloroethyl, chloro-n-propyl, chloro-i-propyl, chloro-n-butyl, chloro-i-butyl, chloro-sec.-butyl, chloro-tert.-butyl, bromomethyl, bromoethyl, bromo-n-propyl, bromo-i-propyl, bromo-n-butyl, bromo-i-butyl, bromo-sec.-butyl and bromo-tert.-butyl, and A is an optionally substituted alkanediyl with 1 to 6 carbon atoms the substituents being selected from the group consisting of alkyl with 1 to 4 carbon atoms, by a radical selected from selected from the group consisting of fluorine, chlorine, bromine, nitro, alkyl with 1 to 4 carbon atoms, halogenoalkyl with 1 to 4 carbon atoms or halogenoalkoxy with 1 to 4 carbon atoms.

2. A compound as claimed in claim 1, wherein
R is methyl, ethyl, n-propyl, i-propyl, n-butyl, i-butyl, sec.-butyl, tert.-butyl, chloromethyl, chloroethyl, chloro-n-propyl, chloro-i-propyl, chloro-n-butyl, chloro-i-butyl, chloro-sec.-butyl, chloro-tert.-butyl, bromomethyl, bromoethyl, bromo-n-propyl, bromo-i-propyl, bromo-n-butyl, bromo-i-butyl, bromo-sec.-butyl and bromo-tert.-butyl, and
A is alkanediyl with 1 or 2 carbon atoms or substituted alkanediyl with 1 or 2 carbon atoms, the substituents alkanediyl with 1 or 2 carbon atoms, the substituents being selectd from alkyl with 1 to 4 carbon atoms, phenyl or phenyl mono-substituted by a radical selected from selected from the group consisting of fluorine, chlorine, bromine, nitro, alkyl with 1 to 4 carbon atoms, alkoxy with 1 to 4 carbon atoms, trifluoromethyl or trifluoromethoxy.

3. A compound as claimed in claim 1, having the formula

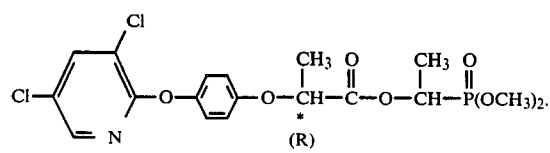

4. A compound as claimed in claim 1, having the following formula

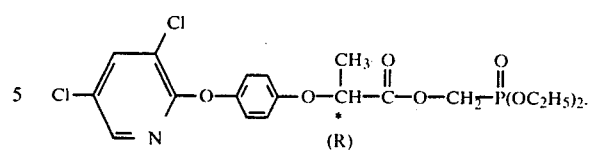

5. A phenoxypropionyloxyalkanephosphate of the formula:

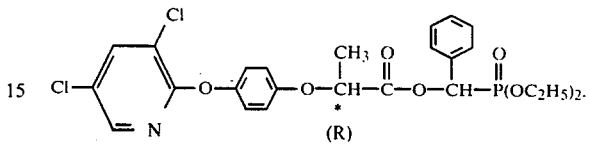

6. A herbicidal composition comprising an agriculturally acceptable carrier and, in herbicidally effective amount, a phenoxypropionyloxyalkanephosphonate as claimed in claim 1.

7. A herbicidal composition as claimed in claim 6, comprising from 0.1 to 95% by weight of the active compound.

8. A method of combating weeds, which comprises applying to the weeds, or to their habitat, a herbicidally effective amount of a phenoxypropionyloxyalkanephosphonate as claimed in claim 1.

9. A method as claimed in claim 8, wherein said compound is applied at a dosage of 0.05 to 10 kg per hectare.

10. A method as claimed in claim 8, wherein said phenoxypropionyloxyalkanephosphonate is selected from the compounds of the formulae

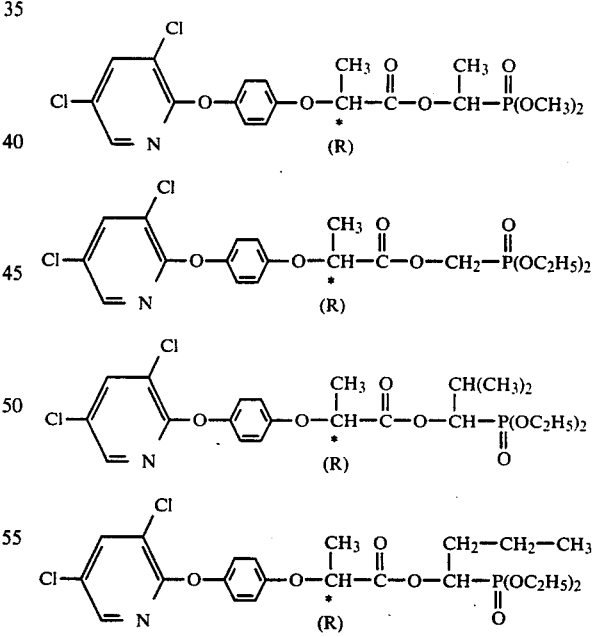

and

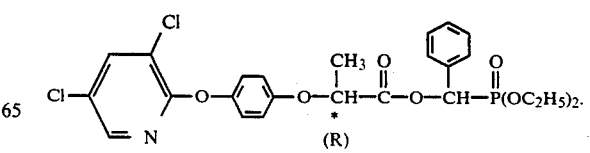

UNITED STATES PATENT AND TRADEMARK OFFICE
CERTIFICATE OF CORRECTION

PATENT NO. : 4,670,040
DATED : June 2, 1987
INVENTOR(S) : Theodor Pfister, et al.

It is certified that error appears in the above-identified patent and that said Letters Patent is hereby corrected as shown below:

| | |
|---|---|
| Title Page, No. "[54]" and Col. 1, lines 3 and 4 | Delete title and substitute --R-ENANTIOMERS OF DICHLORO-PYRIDYLOXY-PHENOXY-PROPIONATE-PHOSPHONATES HAVING HERBICIDAL ACTIVITY-- |
| Col. 1, line 6 | Correct spelling of --pionyloxyalkanephosphonates-- |
| Col. 1, line 40 | Correct spelling of --which-- |
| Col. 1, line 41 | Correct spelling of --dichloropyridin-- |
| Col. 2, line 62 | Correct spelling of --fluoromethoxy-- |
| Col. 16, line 11 | Delete "ylozy" and substitute --yloxy-- |
| Col. 17, line 34 | After "4 carbon atoms" insert --phenyl or phenyl mono-substituted-- |
| Col. 17, line 49 | Delete "alkanediyl with 1 or 2 carbon atoms, the substituents" as being redundant |
| Col. 17, line 50 | Delete "selectd" and substitute --selected-- |

UNITED STATES PATENT AND TRADEMARK OFFICE
CERTIFICATE OF CORRECTION

PATENT NO. : 4,670,040

DATED : June 2, 1987

INVENTOR(S) : Theodor Pfister, et al.

It is certified that error appears in the above-identified patent and that said Letters Patent is hereby corrected as shown below:

Col. 17, line 50     Delete "selectd" and substitute --selected--

Signed and Sealed this

Third Day of May, 1988

Attest:

DONALD J. QUIGG

Attesting Officer

Commissioner of Patents and Trademarks